US00PP21462P2

(12) United States Plant Patent
Morgan

(10) Patent No.: US PP21,462 P2
(45) Date of Patent: Nov. 9, 2010

(54) ***PHORMIUM* PLANT NAMED 'ELECTRIC BLACK LIGHT'**

(50) Latin Name: *Phormium tenax*
Varietal Denomination: Electric Black Light

(76) Inventor: Mal Morgan, 63 Mills Road, Macquarie Fields NSW (AU)

( * ) Notice: Subject to any disclaimer, the term of this patent is extended or adjusted under 35 U.S.C. 154(b) by 0 days.

(21) Appl. No.: 12/460,421

(22) Filed: Jul. 18, 2009

(51) Int. Cl.
*A01H 5/00* (2006.01)

(52) U.S. Cl. ..... Plt./373
(58) Field of Classification Search ..... Plt./373
See application file for complete search history.

*Primary Examiner*—Kent L Bell

(57) ABSTRACT

A new and distinct *Phormium* cultivar named 'Electric Black Light' is disclosed, characterized by compact growth habit, overall short plant height, with very densely forming clumps. The new cultivar has extremely dark foliage color, with a slight waxiness, consistently dark in color, resisting change under heat or drought. The new cultivar is a *Phormium*, typically suited for garden and ornamental container use.

1 Drawing Sheet

Figure 1:
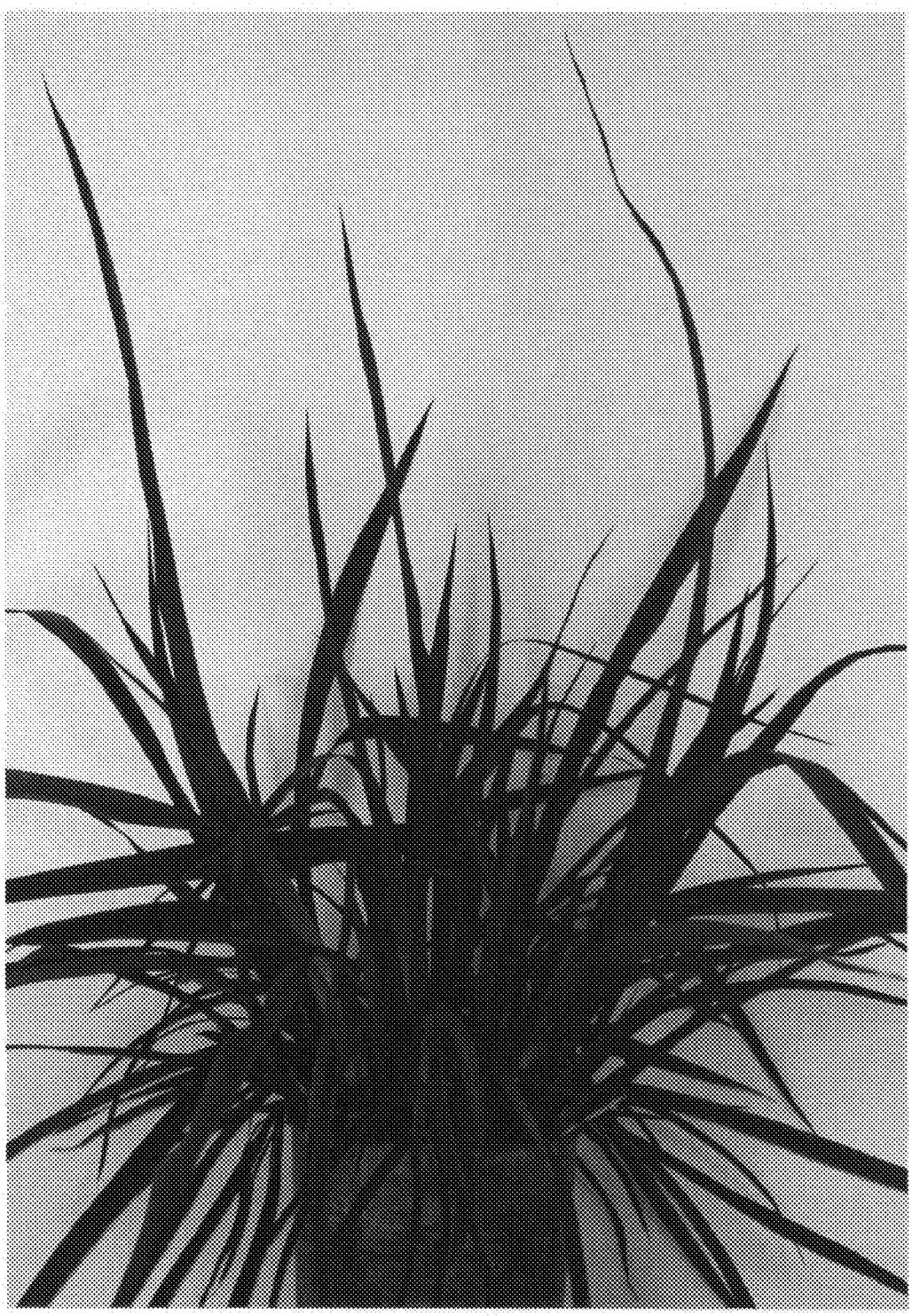

Latin name of the genus and species: *Phormium tenax*.
Variety denomination: 'Electric Black Light'.

BACKGROUND OF THE INVENTION

The new cultivar is the result of a commercial breeding programmed developed with the intent to create new *Phormium* varieties in interesting colors with more compact plant sizes. 'Electric Black Light' was discovered by the inventor, Mal Morgan, a citizen of Australia in October of 2004 at a commercial nursery in Australia. The new cultivar resulted from a crossing performed by the inventor in 2002.

The seed parent is an unpatented, unnamed, proprietary seedling of *Phormium tenax*. The pollen parent is also an unpatented, unnamed proprietary seedling of *Phormium tenax*.

Asexual reproduction of the new cultivar 'Electric Black Light' was first performed in Macquarie Fields, Australia by micropropagation tissue culture in October of 2004. Subsequently, at least 7 generations of 'Electric Black Light' have been reproduced and have shown that the unique features of this cultivar are stable and reproduced true to type.

SUMMARY OF THE INVENTION

The cultivar 'Electric Black Light' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Electric Black Light' These characteristics in combination distinguish 'Electric Black Light' as a new and distinct *Phormium* cultivar:

1. Compact growth habit.
2. Overall short plant height, with very densely forming clumps.
3. Extremely dark foliage color.
4. Consistently dark foliage color, resisting change under heat or drought.
5. Strong new clump formation
6. Waxy texture to the top surface of the foliage. .

COMPARISON TO PARENT

Plants of the new cultivar 'Electric Black Light' are similar to plants of both the seed parent, and pollen parent in most horticultural characteristics, however, 'Electric Black Light' has darker foliage, with a slight waxiness, not seen in either parent variety. Additionally, plants of the new variety produce more new clumps than plants of either parent.

COMMERCIAL COMPARISON

Plants of the new cultivar 'Electric Black Light' can be compared to the unpatented commercial variety *Phormium tenax* 'Platt's Black'. Plants of 'Platt's Black' have a similar foliage coloration. However, plants of the new cultivar 'Electric Black Light' produce more clumps per plant, and have a waxy coating on the surface of the leaf.

BRIEF DESCRIPTION OF THE PHOTOGRAPH

The accompanying photograph in FIG. 1 illustrates in full color a typical plant of 'Electric Black Light' grown outdoors in Lompoc, Calif. This plant is approximately 1 year old, shown in a 1 gallon nursery container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Electric Black Light' plants grown in a greenhouse in Lompoc, Calif. Temperatures ranged from 10° C. to 20° C. at night to 12° C. to 25° C. during the day. No artificial light, photoperiodic treatments or chemical treatments were given to the plants. Measurements and numerical values represent averages of typical plant types.

Botanical classification: *Phormium tenax* 'Electric Black Light'.

PLANT

Growth habit: Upright, evergreen perennial.
Plant shape: Inverted triangle.
Height: Approximately 55 cm.
Plant spread: Approximately 72 cm.
Branching characteristics: Herbaceous shoots emerging basally.
Number of clumps per plant: Approximately 5 distinctive basal clumps, growing very densely together, in an approximately 1 year old plant.
Age of plant described: Approximately 1 year.
Roots: Moderately dense, thicky, fleshy with, slightly fibrous secondary roots. Color near RHS Yellow-white 158 D.

FOLIAGE

Leaf:
*Arrangement.*—Cauline.
*Compound or single.*—Single.
*Quantity of leaves per clump.*—15.
*Average length.*—Approximately 58 cm.
*Average width.*—Approximately 2.8 cm.
*Shape of blade.*—Linear.
*Aspect.*—Arching.
*Apex.*—Long acuminate.
*Base.*—Cuneate.
*Margin.*—Entire.
*Texture of top surface.*—Glabrous, with waxiness, finely ridged.
*Texture of bottom surface.*—Glabrous, finely ridged.
*Pubescence.*—Entirely non-pubescent.
*Color.*—Young foliage upper side: Near R.H.S. Greyed-Purple N186B. Young foliage under side: Near R.H.S. Greyed-Purple N186B with occasional stripes near Greyed-Purple N186C. Mature foliage upper side: Near R.H.S. Greyed-Purple N186A. Mature foliage under side: Near R.H.S. Greyed-Purple N186A.
*Venation.*—Type: Parallel with 1 prominent, very thin mid-vein. Width of mid vein: Approximately 0.1 cm.
*Venation coloration upper side.*—Near R.H.S. Greyed-Purple N186D, mid vein Greyed-Purple 185A.
*Venation coloration under side.*—Near R.H.S. Greyed-Purple N186A.
Petiole: Not present.

INFLORESCENCE

Flowering has not been observed to date and is not commercially important in this cultivar.

OTHER CHARACTERISTICS

Disease resistance: Neither resistance nor susceptibility to diseases or pests has been observed in this variety.
Drought tolerance and cold tolerance: Observed to tolerate temperatures to 40° C. without any negative effects. Low temperatures near −5° C. will cause foliage damaged, and prolonged exposure will probably kill the plant. Once established, plants tolerate drought, requiring little or no supplemental water.
Fruit/seed production: Not observed to date.

What is claimed is:

1. A new and distinct cultivar of *Phormium* plant named 'Electric Black Light' as herein illustrated and described.

* * * * *